(12) United States Patent
Laas et al.

(10) Patent No.: US 9,556,304 B2
(45) Date of Patent: Jan. 31, 2017

(54) BINDER WITH CYCLIC CARBONATE STRUCTURES

(71) Applicant: Covestro Deutschland AG, Leverkusen (DE)

(72) Inventors: Hans-Josef Laas, Odenthal (DE); Dorota Greszta-Franz, Solingen (DE); Berta Vega Sanchez, Köln (DE)

(73) Assignee: Covestro Deutschland AG, Leverkusen (DE)

( * ) Notice: Subject to any disclaimer, the term of this patent is extended or adjusted under 35 U.S.C. 154(b) by 31 days.

(21) Appl. No.: 14/424,561

(22) PCT Filed: Aug. 22, 2013

(86) PCT No.: PCT/EP2013/067463
§ 371 (c)(1),
(2) Date: Feb. 27, 2015

(87) PCT Pub. No.: WO2014/033045
PCT Pub. Date: Mar. 6, 2014

(65) Prior Publication Data
US 2015/0203623 A1    Jul. 23, 2015

(30) Foreign Application Priority Data
Aug. 28, 2012 (EP) .................................. 12182068

(51) Int. Cl.
| C08G 18/71 | (2006.01) |
| C07D 317/36 | (2006.01) |
| C08G 18/62 | (2006.01) |
| C08G 18/68 | (2006.01) |
| C08G 18/80 | (2006.01) |
| C09D 175/04 | (2006.01) |
| C08G 18/42 | (2006.01) |

(52) U.S. Cl.
CPC ........... *C08G 18/714* (2013.01); *C07D 317/36* (2013.01); *C08G 18/42* (2013.01); *C08G 18/4219* (2013.01); *C08G 18/4227* (2013.01); *C08G 18/6254* (2013.01); *C08G 18/68* (2013.01); *C08G 18/8064* (2013.01); *C09D 175/04* (2013.01)

(58) Field of Classification Search
CPC .................................................. C08G 18/8064
USPC ........................................................ 525/454
See application file for complete search history.

(56) References Cited

U.S. PATENT DOCUMENTS

| 3,640,967 | A | 2/1972 | Konig et al. |
| 4,218,543 | A | 8/1980 | Weber et al. |
| 4,835,289 | A | 5/1989 | Brindopke |
| 5,126,170 | A | 6/1992 | Zwiener et al. |
| 5,688,891 | A | 11/1997 | Hovestadt et al. |
| 5,861,107 | A | 1/1999 | Buysch et al. |
| 6,428,854 | B1 | 8/2002 | Melchiors et al. |
| 6,544,593 | B1* | 4/2003 | Nagata ............... C08G 18/3851 427/385.5 |
| 6,730,768 | B2 | 5/2004 | Heidbreder et al. |
| 7,790,908 | B2 | 9/2010 | Schmitt et al. |
| 8,118,968 | B2 | 2/2012 | Moeller et al. |
| 2003/0050424 | A1* | 3/2003 | Bernard ............... C07D 317/34 528/49 |

(Continued)

FOREIGN PATENT DOCUMENTS

| DE | 1770245 A1 | 10/1971 |
| DE | 2622951 A1 | 11/1977 |

(Continued)

OTHER PUBLICATIONS

King Industries. K-Flex 188. Evidentiary Reference. Available at http://www.kingindustries.com/products/k-flex-188/. Accessed May 19, 2016.*

(Continued)

*Primary Examiner* — Mike M Dollinger
(74) *Attorney, Agent, or Firm* — John E. Mrozinski, Jr.

(57) ABSTRACT

The invention relates to a method for producing polyurethanes containing cyclic carbonate structures by reacting at least A) a composition containing a) one or more compounds of the general formula (I), said compounds containing isocyanate groups and cyclic carbonate structures, and b) <=1 wt. %, based on the total mass of the composition A), of one or more monomer diisocyanates with aliphatically, cycloaliphatically, araliphatically, and/or aromatically bound isocyanate groups of the general formula (II), wherein R represents hydrogen or a saturated or unsaturated, linear or branched, aliphatic group with 1 to 7 carbon atoms, X represents a linear or branched organic group which comprises 1 to 36 carbon atoms and which can contain optionally ether, ester, and/or carbonate groups, n represents 0 or 1, and Y represents a linear or branched, aliphatic or cycloaliphatic group with 4 to 18 carbon atoms or an optionally substituted aromatic or aliphatic group with 6 to 18 carbon atoms, with B) an at least difunctional polyol with a number-average molecular weight Mn of 62 to 22000 g/mol, preferably 90 to 12000 g/mol, while maintaining an equivalent ratio of isocyanate groups to hydroxyl groups of 0.3:1 to 1.2:1. Furthermore, the invention relates to products which can be obtained using the method according to the invention. The invention additionally relates to the use of the products which can be obtained using the method according to the invention as a starting component in the production of crosslinkable binders, such as paints and raw materials for sealants or adhesives.

16 Claims, No Drawings

(56) References Cited

U.S. PATENT DOCUMENTS

| | | | |
|---|---|---|---|
| 2009/0092801 A1* | 4/2009 | Sato | C08G 18/0823 428/195.1 |
| 2010/0137507 A1 | 6/2010 | Bernard et al. | |
| 2012/0245241 A1 | 9/2012 | Peiffer et al. | |

FOREIGN PATENT DOCUMENTS

| | | |
|---|---|---|
| DE | 196 25 265 A1 | 1/1998 |
| DE | 19701835 A1 | 7/1998 |
| EP | 0 229 622 A2 | 7/1987 |
| EP | 0328150 A2 | 8/1989 |
| EP | 0403921 A2 | 12/1990 |
| EP | 0659792 A2 | 6/1995 |
| EP | 0689556 A1 | 1/1996 |
| EP | 0 703 230 A1 | 3/1996 |
| EP | 0 739 888 A1 | 10/1996 |
| EP | 0 911 352 A2 | 4/1999 |
| EP | 0937110 A1 | 8/1999 |
| EP | 0978523 A1 | 2/2000 |
| EP | 0 983 231 A1 | 3/2000 |
| EP | 1767559 A1 | 3/2007 |
| EP | 1 963 301 A1 | 9/2008 |
| EP | 2046861 A1 | 4/2009 |
| WO | WO-03016298 A2 | 2/2003 |
| WO | WO-2006/010408 A1 | 2/2006 |
| WO | WO-2008125419 A1 | 10/2008 |
| WO | WO-2011/069966 A1 | 6/2011 |
| WO | WO-2011/124710 A1 | 10/2011 |
| WO | WO-2011159219 A1 | 12/2011 |

OTHER PUBLICATIONS

Machine Translation of EP 328150.*
International Search Report for PCT/EP2013/067463 mailed Oct. 22, 2013.

* cited by examiner

BINDER WITH CYCLIC CARBONATE STRUCTURES

CROSS-REFERENCE TO RELATED APPLICATIONS

This application is a national stage application (under 35 U.S.C. §371) of PCT/EP2013/067463, filed Aug. 22, 2013, which claims benefit of European Application No. 12182068.2, filed Aug. 28, 2012, both of which are incorporated herein by reference in their entirety.

The invention relates to a process for preparing polyurethanes containing cyclic carbonate structures, to the polyurethanes containing cyclic carbonate structures obtainable by this process, to the use thereof as binders in crosslinkable raw materials for varnishes, sealants or adhesives, and to the crosslinkable binders containing the inventive structures.

Polyurethanes bearing cyclic carbonate groups have long been known and have been described many times as binders for adhesives, sealants or coatings.

A very simple, frequently utilized method for preparation of such polyurethanes involves the reaction of low molecular weight hydroxy-functional cyclic carbonates with polyisocyanates or isocyanate-functional prepolymers.

For example, WO 2006/010408 describes isocyanate-free reaction products of linear polyurethane prepolymers based on diphenylmethane diisocyanate (MDI) with 4-(hydroxymethyl)-1,3-dioxolan-2-one (glycerol carbonate), which can be crosslinked even at room temperature with compounds bearing at least two primary or secondary amino groups. Such two-component binders find use as adhesives and sealants, especially as laminating adhesive for composite films.

Polyisocyanates blocked with hydroxy-functional cyclic carbonates, for example reaction products of polyisocyanurate polyisocyanates of 1,6-diisocyanatohexane (hexamethylene diisocyanate, HDI) with glycerol carbonate, are provided by WO 2008/125419. Dissolved in specific acetals, such as 1,1,2,2-tetramethoxyethane in particular, such glycerol carbonate/polyisocyanate adducts with polyether polyamines or polyamide amines likewise cure even at room temperature to give varnish films of high optical quality.

Compounds bearing cyclic carbonate groups can also be combined with hydroxy-functional co-reactants. While the aminic curing of the cyclic carbonate groups proceeds with sufficient speed even at low temperatures, crosslinking in this case, however, takes place only at elevated temperatures, generally under baking conditions, and in the presence of specific catalysts.

EP-A 0 911 352 describes, for example, one-component systems that are storage-stable at room temperature, consisting of polyols, reaction products of polyisocyanurate polyisocyanates of HDI and/or of 1-isocyanato-3,3,5-trimethyl-5-isocyanatomethylcyclohexane (isophorone diisocyanate, IPDI) with 5-(hydroxymethyl)-5-ethyl-1,3-dioxan-2-one (IMP carbonate) as crosslinker components and specific metal carboxylates as curing catalysts, which can be baked at elevated temperatures to give hard solvent-resistant coatings without elimination of volatile compounds.

The preparation of oligourethanes containing 1,3-dioxan-2-one groups from diisocyanates or polyisocyanates using TMP carbonate and the use thereof as crosslinkers for polyols in thermally curable coating systems is also known from EP-A 0 703 230.

The reactive systems that are based on hydroxy-functional cyclic carbonates and are known nowadays are therefore reaction products of such units either with oligomeric polyisocyanates of comparatively low molecular weight or with isocyanate prepolymers of relatively high molecular weight, although these are generally of linear structure. Polyisocyanate components that are of high molecular weight and simultaneously of high functionality have not been described to date as co-reactants for hydroxy-functional cyclocarbonates. However, specifically polymeric polycyclocarbonate polyurethanes of high molecular weight should be of particular interest as binder components since they should react, for example, in combination with the low molecular weight polyamines of good commercial availability, as serve, for example, as crosslinkers for epoxy systems, to give highly crosslinked, particularly stable polyurethanes.

The main cause of the lack of polymeric polycyclocarbonate polyurethanes of high functionality to date is that low-monomer NCO prepolymers of branched polyols of high molecular weight gelate because of the unavoidable onset of crosslinking reactions during the prepolymerization reaction with diisocyanates and the associated increase in molecular weight, or at least have extremely high viscosities that would make them unusable as units for a reaction with hydroxy-functional cyclic carbonates.

There was therefore a need for novel polyurethanes having cyclic carbonate structures which are preparable reliably and reproducibly in a simple manner from any desired polyols, i.e. including highly branched polymeric polyols.

It was therefore an object of the present invention to provide a process for preparing low-viscosity polyurethanes bearing cyclic carbonate structures from any desired polyols, which is based on formation components obtainable readily and reproducibly even on the industrial scale. The products obtainable by this process should be suitable for all the fields of use of polyurethanes containing cyclic carbonate structures, especially as binders for adhesives, sealants or coatings.

This object is achieved in accordance with the invention by a process for preparing polyurethanes containing cyclic carbonate structures, by reacting at least A) a composition containing
   a) compounds of the general formula (I) containing one or more isocyanate groups and cyclic carbonate structures

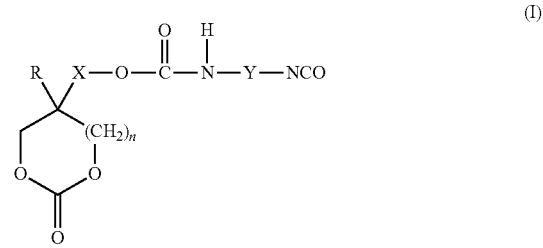

(I)

and b) ≤1% by weight, based on the total mass of the composition A), of one or more monomeric diisocyanates having aliphatically, cycloaliphatically, araliphatically and/or aromatically bonded isocyanate groups of the general formula (II),

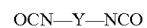

(II)

where
R is hydrogen or a saturated or unsaturated, linear or branched, aliphatic radical having 1 to 7 carbon atoms,
X is a linear or branched organic radical which has 1 to 36 carbon atoms and which may optionally contain ether, ester and/or carbonate groups,
n is 0 or 1 and
Y is a linear or branched, aliphatic or cycloaliphatic radical having 4 to 18 carbon atoms or an optionally substituted aromatic or araliphatic radical having 6 to 18 carbon atoms,
with
B) an at least difunctional polyol having a number-average molecular weight $M_n$ of 62 to 22 000 g/mol, preferably 90 to 12 000 g/mol,
while maintaining a ratio of equivalents of isocyanate groups to hydroxyl groups of 0.3:1 to 1.2:1.

The number-average molecular weights $M_n$ of the polymeric polyols specified in the overall document are determined by means of gel permeation chromatography (GPC) as follows: Calibration is effected with polystyrene standards having molecular weights of Mp 1 000 000 to 162. The eluent used is tetrahydrofuran p.A. The following parameters are observed in the duplicate measurement: measurement at room temperature; degassing: online degasser; flow rate: 1 ml/min; analysis time: 45 minutes; detectors: refractometer and UV detector; injection volume: 100 µl-200 µl. Mean molar mass values $M_n$ are calculated with software support. Baseline points and evaluation limits are fixed in accordance with DIN 55672 Part 1. In the case of low molecular weight polyols having defined structure, the molecular weight calculable from the empirical formula applies.

The process according to the invention is based on the surprising observation that it is possible through reaction of customary hydroxy-functional cyclic carbonates with excess amounts of monomeric diisocyanates and subsequent removal of the unconverted monomers to obtain compounds which simultaneously have an isocyanate group and a cyclic carbonate group, and with which even highly branched polymeric polyols can be converted without any problem to crystallization-stable polyurethanes having cyclocarbonate end groups.

Constituent b) of composition A) has a proportion of ≤1% by weight, preferably ≤0.5% by weight and more preferably ≤0.3% by weight of the total mass of composition A).

In a preferred embodiment of the process according to the invention, composition A) additionally contains compounds (c) of the general formula (III)

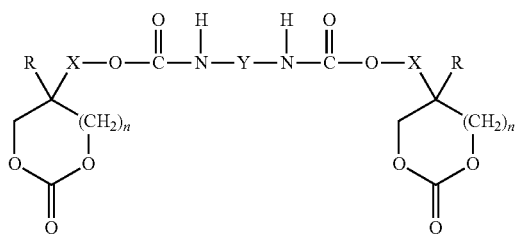

(III)

in an amount of 0.5% to 12% by weight, preferably 0.5% to 10% by weight, based on the total mass of components a) and c), where
R is hydrogen or a saturated or unsaturated, linear or branched, aliphatic radical having 1 to 7 carbon atoms,
X is a linear or branched organic radical which has 1 to 36 carbon atoms and which may optionally contain ether, ester and/or carbonate groups,
n is 0 or 1 and
Y is a linear or branched, aliphatic or cycloaliphatic radical having 4 to 18 carbon atoms or an optionally substituted aromatic or araliphatic radical having 6 to 18 carbon atoms.

In a further preferred embodiment of the process according to the invention, composition A) contains
a) ≥88% by weight, preferably ≥90% by weight and more preferably ≥92% by weight of compounds of the general formula (I),
b) ≤1% by weight, preferably ≤0.5% by weight, more preferably ≤0.3% by weight, of one or more monomeric diisocyanates having aliphatically, cycloaliphatically, araliphatically and/or aromatically bonded isocyanate groups of the general formula (II) and
c) ≤12% by weight, preferably ≤10% by weight and more preferably ≤8% by weight of compounds of the general formula (III),
where the proportion of each of a) and c) relates to the total mass of the compounds a) and c), and the proportion of b) relates to the total mass of the composition A),
and where
R is hydrogen or a saturated or unsaturated, linear or branched, aliphatic radical having 1 to 7 carbon atoms,
X is a linear or branched organic radical which has 1 to 36 carbon atoms and which may optionally contain ether, ester and/or carbonate groups,
n is 0 or 1 and
Y is a linear or branched, aliphatic or cycloaliphatic radical having 4 to 18 carbon atoms or an optionally substituted aromatic or araliphatic radical having 6 to 18 carbon atoms.

Composition A) is preferably obtained by reacting monomeric diisocyanates having aliphatically, cycloaliphatically, araliphatically and/or aromatically bonded isocyanate groups i) with hydroxy-functional cyclic carbonates ii) in a ratio of equivalents of isocyanate groups to hydroxyl groups of at least 8:1, preferably at least 10:1 and more preferably at least 12:1.

Compounds which contain isocyanate groups and cyclic carbonate structures and which have been prepared using a smaller excess of diisocyanate and are as described, for example, in EP-A 0 703 230 and EP-A 0 328 150, in contrast to the compositions A) used in accordance with the invention, in the event of analogous reaction with polyols, always give turbid polycyclocarbonate polyurethanes unusable as binders for varnishes and coatings because they have an excessively high proportion of 2:1 bisadduct of hydroxy-functional cyclic carbonate and diisocyanate.

Suitable starting compounds i) for the preparation of the composition A) are any desired diisocyanates which have aliphatically, cycloaliphatically, araliphatically and/or aromatically bonded isocyanate groups and can be prepared by any desired processes, for example by phosgenation or by a phosgene-free route, for example by urethane cleavage.

Suitable diisocyanates are, for example, those of the general formula (II)

$$OCN-Y-NCO$$ (II)

in which Y is a linear or branched, aliphatic or cycloaliphatic radical having 4 to 18 carbon atoms or an optionally substituted aromatic or araliphatic radical having 6 to 18 carbon atoms, for example 1,4-diisocyanatobutane, 1,6-diisocyanatohexane (HDI), 1,5-diisocyanato-2,2-dimethylpentane, 2,2,4- or 2,4,4-trimethyl-1,6-diisocyanatohexane, 1,10-diiisocyanatodecane, 1,3- and 1,4-diisocyanatocyclohexane, 1,4-diisocyanato-3,3,5-trimethylcyclohexane, 1,3-diisocyanato-2-methylcyclohexane, 1,3-diisocyanato-4-methylcyclohexane, 1-isocyanato-3,3,5-trimethyl-5-isocyanatomethylcyclohexane (isophorone diisocyanate; IPDI), 1-isocyanato-1-methyl-4(3)-isocyanatomethylcyclohexane, 2,4'- and 4,4'-diisocyanatodicyclohexylmethane ($H_{12}$-MDI), 1,3- and 1,4-bis(isocyanatomethyl)cyclohexane, 4,4'-diisocyanato-3,3'-dimethyldicyclohexylmethane, 4,4'-diisocyanato-3,3',5,5'-tetramethyldicyclohexylmethane, 4,4'-diisocyanato-1,1'-bi(cyclohexyl), 4,4'-diisocyanato-3,3'-dimethyl-1,1'-bi(cyclohexyl), 4,4'-diisocyanato-2,2',5,5'-tetramethyl-1,1'-bi(cyclohexyl), 1,8-diisocyanato-p-menthane, 1,3-diisocyanatoadamantane, 1,3- dimethyl-5,7-diisocyanatoadamantane, 1,3- and 1,4-bis(isocyanatomethyl)benzene (XDI), 1,3- and 1,4-bis(1-isocyanato-1-methylethyl)benzene (TMXDI), bis(4-(1-isocyanato-1-methylethyl)phenyl) carbonate, phenylene 1,3- and 1,4-diisocyanate, tolylene 2,4- and 2,6-diisocyanate (TDI) and any desired mixtures of these isomers, diphenylmethane 2,4'- and/or 4,4'-diisocyanate (MDI) and naphthylene 1,5-diisocyanate (NDI) and any desired mixtures of such diisocyanates.

Further diisocyanates that are likewise suitable can additionally be found, for example, in Justus Liebigs Annalen der Chemie, volume 562 (1949) p. 75-136.

Preferred starting components i) are diisocyanates of the general formula (II) in which Y is a linear or branched, aliphatic or cycloaliphatic radical having 6 to 13 carbon atoms.

Particularly preferred starting components i) are 1,6-diisocyanatohexane, 1-isocyanato-3,3,5-trimethyl-5-isocyanatomethylcyclohexane, 2,4'- and/or 4,4'-diisocyanatodicyclohexylmethane or mixtures thereof.

Suitable starting components ii) for preparation of the composition A) are hydroxy-functional cyclic carbonates of the general formula (IV) or mixtures thereof

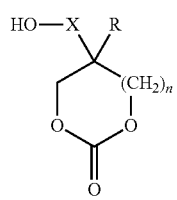

(IV)

in which

R is hydrogen or a saturated or unsaturated, linear or branched, aliphatic radical having 1 to 7 carbon atoms, X is a linear or branched organic radical which has 1 to 36 carbon atoms and which may optionally contain ether, ester and/or carbonate groups, and n is 0 or 1.

Suitable starting components ii) are, for example, simple hydroxy-functional cyclocarbonates, for example 4-(hydroxymethyl)-1,3-dioxolan-2-one (glycerol carbonate), 5-(hydroxymethyl)-5-methyl-1,3-dioxan-2-one and/or 5-(hydroxymethyl)-5-ethyl-1,3-dioxan-2-one (TMP carbonate).

Suitable starting components ii) are additionally also the polyether alcohols, polyester alcohols and/or polycarbonate alcohols which have number-average molecular weights $M_n$ of up to 600 g/mol, preferably up to 500 g/mol, more preferably up to 400 g/mol, have cyclic carbonate structures and are obtainable by known methods through reaction of these simple hydroxy-functional cyclic carbonates with alkylene oxides, for example ethylene oxide and/or propylene oxide, lactones, for example β-propiolactone, γ-butyrolactone, δ-valerolactone, ε-caprolactone, 3,5,5- and 3,3,5-trimethylcaprolactone, and/or cyclic carbonates, for example 1,3-dioxan-2-one (trimethylene carbonate) and 5,5-dimethyl-1,3-dioxan-2-one (neopentyl glycol carbonate).

The preparation of the starting compounds ii) does not form part of the subject matter of the present application. They can be obtained by known processes, for example using fossil fuels or else from renewable raw materials, for example from biogenic glycerol, as obtained, for example, as a coproduct of biodiesel production.

Examples of possible preparation processes for the abovementioned simple hydroxy-functional cyclic carbonates include reactions of glycerol or trimethylolpropane with ethylene carbonate, dialkyl carbonates or diaryl carbonates, for example dimethyl or diphenyl carbonate, under transesterification conditions (see, for example, EP-A 1 963 301, EP-A 0 739 888, DE-A 196 25 265 and WO 2011/159219). In addition, glycerol carbonate can also be obtained by direct reaction of glycidol with carbon dioxide in the presence of suitable catalysts (see, for example, EP-A 0 229 622).

Processes for preparing the compounds which are likewise suitable as starting compounds ii) and which additionally contain at least one polyether, polyester and/or polycarbonate group are likewise already known.

For example, the reaction of simple hydroxy-functional cyclic carbonates with alkylene oxides, especially with propylene oxide, by the standard methods for synthesis of polyethers (see, for example, N. Adam et al.: "Polyurethanes", Ullmann's Encyclopedia of Industrial Chemistry, Electronic Release, 7th ed., chap. 3.2.1, Wiley-VCH, Weinheim 2005) in the presence of KOH or especially by the IMPACT process using double metal cyanide catalysts (DMC) gives polyether alcohols which have cyclic carbonate structures in terminal positions and are suitable as starting compound ii).

Preferred starting compounds ii) having at least one ether group are those of the abovementioned molecular weight range based on glycerol carbonate and propylene oxide.

Suitable starting compounds ii) containing at least one ester group as well as a cyclic carbonate group can be prepared in a manner known per se from lactones and the above-described simple hydroxy-functional cyclic carbonates as starter molecules with ring opening. Suitable lactones for preparation of these starting compounds ii) containing ester groups are, for example, β-propiolactone, γ-butyrolactone, δ-valerolactone, ε-caprolactone, 3,5,5- and 3,3,5-trimethylcaprolactone or any desired mixtures of such lactones.

Preferred starting compounds ii) having at least one ester group are those of the abovementioned molecular weight range based on glycerol carbonate and ε-caprolactone.

Finally, likewise suitable as starting compounds ii) are also compounds containing at least one further carbonate group as well as a cyclic carbonate group. Compounds of this kind are likewise already known and are obtainable, for example, by the process described in Example 1), Step (A) of WO 03/016298 through reaction of the above-described simple hydroxy-functional cyclic carbonates with trimethylene carbonate and/or neopentyl glycol carbonate.

Preferred starting compounds ii) having at least one carbonate group are those of the abovementioned molecular weight range based on glycerol carbonate and neopentyl glycol carbonate.

In general, the above-described starting compounds ii) containing at least one ester group and/or at least one further carbonate group as well as a cyclic carbonate group are prepared by ring-opening polymerization in the presence of catalysts, for example Lewis or Brønsted acids, organic tin or titanium compounds, at temperatures of 20 to 200° C., preferably 50 to 160° C.

Further preferred starting components ii) are hydroxy-functional cyclic carbonates of the general formula (IV), or mixtures thereof, in which R is hydrogen or a saturated linear aliphatic radical having 1 or 2 carbon atoms, X is a linear or branched organic radical which has 1 to 18 carbon atoms and which may optionally contain ether, ester and/or carbonate groups, and n is 0 or 1.

Particularly preferred starting components ii) are hydroxy-functional cyclic carbonates of the general formula (IV), or mixtures thereof, in which R is hydrogen or a saturated linear aliphatic radical having 1 or 2 carbon atoms, X is a methylene group (—$CH_2$—) and n is 0 or 1.

A very particularly preferred starting component ii) is glycerol carbonate.

The hydroxy-functional cyclic carbonates ii) can be used either individually or in the form of any desired mixtures with one another.

For preparation of the composition A), the diisocyanates 1) are preferably reacted with at least one hydroxy-functional cyclic carbonate ii) at temperatures of 20 to 200° C., preferably 40 to 160° C.

Component i) is reacted with component ii) preferably in a ratio of equivalents of isocyanate groups to hydroxyl groups of at least 8:1, preferably at least 10:1 and more preferably at least 12:1. Likewise preferably, component i) is reacted with component ii) in a ratio of equivalents of isocyanate groups to hydroxyl groups of not more than 40:1, preferably of not more than 30:1.

The reaction of the starting components i) and ii) can be executed in solution or without solvent in substance, but is preferably executed without solvent.

The reaction can be conducted without catalysis. The reaction can optionally also be accelerated using customary catalysts known from polyurethane chemistry. Examples include tertiary amines, for example triethylamine, tributylamine, dimethylbenzylamine, diethylbenzylamine, pyridine, methylpyridine, dicyclohexylmethylamine, dimethylcyclohexylamine, N,N,N',N'-tetramethyldiaminodiethyl ether, bis(dimethylaminopropyl)urea, N-methyl- or N-ethylmorpholine, N-cocomorpholine, N-cyclohexylmorpholine, N,N,N',N'-tetramethylethylenediamine, N,N,N',N', tetramethyl-1,3-butanediamine, N,N,N',N'-tetramethyl-1,6-hexanediamine, pentamethyldiethylenetriamine, N-methylpiperidine, N-dimethylaminoethylpiperidine, N,N'-dimethylpiperazine, N-methyl-N'-dimethylaminopiperazine, 1,2-dimethylimidazole, 2-methylimidazole, N,N-dimethylimidazole-β-phenylethylamine, 1,4-diazabicyclo[2.2.2]octane (DABCO) and bis(N,N-dimethylaminoethyl) adipate, amidines, for example 1,5-diazabicyclo[4.3.0]non-ene (DBN), 1,8-diazabicyclo(5.4.0)undec-7-ene (DBU) and 2,3-dimethyl-3,4,5,6-tetrahydropyrimidine, alkanolamine compounds, for example triethanolamine, triisopropanolamine, N-methyldiethanolamine, N-ethyldiethanolamine, dimethylaminoethanol and 2-(N,N-dimethylaminoethoxy)ethanol, N,N',N"-tris(dialkylaminoalkyl) hexahydrotriazine, for example N,N',N"-tris (dimethylaminopropyl)-s-hexahydrotriazine, bis (dimethylaminoethyl) ether and metal salts, for example inorganic and/or organic compounds of iron, lead, bismuth, zinc and/or tin in customary oxidation states of the metal, for example iron(II) chloride, iron(III) chloride, bismuth(III) bismuth(III) 2-ethylhexanoate, bismuth(III) octoate, bismuth(III) neodecanoate, zinc chloride, zinc 2-ethylcaproate, tin(II) octoate, tin(II) ethylcaproate, tin(II) palmitate, dibutyltin(IV) dilaurate (DBTL), dibutyltin(IV) dichloride or lead octoate.

Catalysts for use with preference are tertiary amines, tin compounds, zinc compounds and bismuth compounds of the type specified.

The catalysts mentioned by way of example can be used individually or in the form of any desired mixtures with one another in the preparation of the composition A) and are used, if at all, in amounts of 0.001% to 1.0% by weight, preferably 0.005% to 0.5% by weight, calculated as the total amount of catalysts used, based on the total amount of starting compounds used.

The progress of the reaction can be monitored by determining the NCO content by titrimetric means, for example. On attainment of the desired NCO content, generally after full urethanization, the reaction is stopped.

In a preferred embodiment, after the conversion of components i) and ii), any unconverted excess of monomeric diisocyanates i) is separated from the reaction product apart from a residual content of ≤1% by weight, preferably of ≤0.5% by weight, more preferably of ≤0.3% by weight, based on the total mass of the reaction product.

This is preferably done by freeing the reaction mixture of excess monomeric diisocyanates i) by thin-film distillation under reduced pressure, for example at a pressure of below 1.0 mbar, preferably below 0.5 mbar, more preferably below 0.2 mbar, under very gentle conditions, for example at a temperature of 100 to 200° C., preferably of 120 to 180° C.

The distillates obtained can be used without any problem for a new reaction with suitable starting compounds ii).

In a further, although less preferred embodiment, the monomeric diisocyanates are separated from the inventive process product formed by extraction with suitable solvents inert toward isocyanate groups, for example aliphatic or cycloaliphatic hydrocarbons such as pentane, hexane, heptane, cyclopentane or cyclohexane.

Irrespective of the type of workup, clear, virtually colorless compositions A) are obtained, and these, depending on the starting diisocyanate chosen, are liquids of low to high viscosity or solid materials and have NCO contents of 4.5% to 14.8% by weight, preferably 5.0% to 14.8% by weight, more preferably 9.0% to 14.5% by weight, and residual contents of monomeric diisocyanates of less than 1.0% by weight, preferably of less than 0.5% by weight, more preferably of less than 0.3% by weight, based on the total mass of the composition A).

As constituent b) of the composition A), it is consequently possible for all the monomeric diisocyanates i) used for preparation of the composition A) to occur. The preferred embodiments specified above for component ii) also apply to b).

For the formulae (I) and (III) of components a) and b), or for the formulae (I), (II) and (III) of components a), b) and c), it is preferable that Y is a linear or branched, aliphatic or cycloaliphatic radical having 6 to 13 carbon atoms.

In addition, for the formula (I) of component a) or the formulae (I) and (III) of components a) and c), it is preferable that R is hydrogen or a saturated linear aliphatic radical having 1 or 2 carbon atoms, X is a linear or branched organic radical which has 1 to 18 carbon atoms and which may optionally contain ether, ester and/or carbonate groups, and n is 0 or 1.

For the formula (I) of component a) or the formulae (I) and (II) of components a) and c), it is more preferable that R is hydrogen or a saturated linear aliphatic radical having 1 or 2 carbon atoms, X is a methylene group (—$CH_2$—) and n is 0 or 1.

The polyol components B) used in the process according to the invention are any desired at least difunctional polyols having a number-average molecular weight $M_n$ of 62 to 22 000 g/mol, preferably 90 to 18 000 g/mol, more preferably 90 to 12 000 g/mol.

Preferably, the polyol components B) used in the process according to the invention have a mean functionality of 2 to 6 and more preferably a mean functionality of 2 to 4.

It is also possible to use any desired mixtures of the polyols mentioned.

In a preferred embodiment of the invention, components B) used are simple polyhydric alcohols, ether alcohols or ester alcohols and/or polymeric polyols, said polymeric polyols having a number-average molecular weight $M_n$ of 200 to 22 000 g/mol, preferably 250 to 18 000 g/mol, more preferably 250 to 12 000 g/mol.

In a specific embodiment of the process according to the invention, polyol components B) used are polyhydric alcohols and/or ether alcohols or ester alcohols containing 2 to 14 carbon atoms, preferably 4 to 10 carbon atoms.

Suitable polyols B) are, for example, simple polyhydric alcohols having 2 to 14 and preferably 4 to 10 carbon atoms, for example ethane-1,2-diol, propane-1,2- and -1,3-diol, the isomeric butanediols, pentanediols, hexanediols, heptanediols and octanediols, decane-1,10-diol, dodecane-1,12-diol, cyclohexane-1,2- and -1,4-diol, cyclohexane-1,4-dimethanol, 1,4-bis(2-hydroxyethoxy)benzene, 2,2-bis(4-hydroxyphenyl)propane (bisphenol A), 2,2-bis(4-hydroxycyclohexyl)propane (perhydrobisphenol), propane-1,2,3-triol, butane-1,2,4-triol, 1,1,1-trimethylolethane, hexane-1,2,6-triol, 1,1,1-trimethylolpropane (TMP), bis(2-hydroxyethyl) hydroquinone, 1,2,4- and 1,3,5-trihydroxycyclohexane, 1,3,5-tris(2-hydroxyethyl) isocyanurate, 3(4),8(9)-bis(hydroxymethyl)tricyclo[$5.2.1.0^{2,6}$]decane, ditrimethylolpropane, 2,2-bis(hydroxymethyl)propane-1,3-dial (pentaerythritol), 2,2,6,6-tetrakis(hydroxymethyl)-4-oxaheptane-1,7-diol (dipentaerythritol), mannitol or sorbitol, low molecular weight ether alcohols, for example diethylene glycol, triethylene glycol, tetraethylene glycol, dipropylene glycol or dibutylene glycol, or low molecular weight ester alcohols, for example neopentyl glycol hydroxypivalate.

In another specific embodiment of the process according to the invention, polyol components B) used are the customary polymeric polyether polyols, polyester polyols, polycarbonate polyols and/or polyacrylate polyols known from polyurethane chemistry, typically having a number-average molecular weight $M_n$ of 200 to 22 000 g/mol, preferably of 250 to 18 000 g/mol, more preferably of 250 to 12 000 g/mol. A broad overview of suitable polymeric polyols B) can be found, for example, in N. Adam et al.: "Polyurethanes", Ullmann's Encyclopedia of Industrial Chemistry, Electronic Release, 7th ed., chap. 3.2-3.4, Wiley-VCH, Weinheim 2005.

Suitable polyether polyols B) are, for example, those of the type specified in DE 26 22 951 B, column 6 line 65 to column 7 line 26, EP-A 0 978 523, page 4 line 45 to page 5 line 14, or WO 2011/069966, page 4 line 20 to page 5 line 23, provided that they meet the specifications made above in terms of functionality and molecular weight. Particularly preferred polyether polyols B) are addition products of ethylene oxide and/or propylene oxide onto propane-1,2-diol, propane-1,3-diol, glycerol, trimethylolpropane, ethylenediamine and/or pentaerythritol, or the polytetramethylene ether glycols which are obtainable by polymerizing tetrahydrofuran, for example according to Angew. Chem. 72, 927 (1960), and have number-average molecular weights of 400 g/mol to 4000 g/mol.

Suitable polyester polyols B) are the, for example, those of the type specified in EP-A 0 978 523, page 5 lines 17 to 47, or EP-A 0 659 792, page 6 lines 32 to 45, provided that they meet the specifications made above in terms of functionality and molecular weight. Particularly preferred polyester polyols are condensation products of polyhydric alcohols, for example ethane-1,2-diol, propane-1,2-diol, diethylene glycol, butane-1,4-diol, hexane-1,6-diol, neopentyl glycol, cyclohexane-1,4-dimethanol, cyclohexane-1,4-diol, perhydrobisphenol, 1,1,1-trimethylolpropane, propane-1,2,3-triol, pentaerythritol and/or sorbitol, with substoichiometric amounts of polybasic carboxylic acids or carboxylic anhydrides, for example succinic acid, adipic acid, sebacic acid, dodecanedioic acid, glutaric anhydride, maleic anhydride, phthalic anhydride, isophthalic acid, terephthalic acid, trimellitic acid, hexahydrophthalic anhydride and/or tetrahydrophthalic anhydride, or those as obtainable in a manner known per se from lactones, for example ε-caprolactone, and simple polyhydric alcohols, for example those mentioned above by way of example, as starter molecules with ring opening.

Suitable polycarbonate polyols B) are especially the reaction products of dihydric alcohols known per se, for example those as mentioned by way of example above in the list of polyhydric alcohols, with diaryl carbonates, for example diphenyl carbonate, dimethyl carbonate or phosgene. Suitable polycarbonate polyols B) are also those which additionally contain ester groups as well as carbonate structures. These are especially the polyester carbonate diols known per se, as obtainable, for example, according to the teaching of DE-B 1 770 245 through reaction of dihydric alcohols with lactones, such as ε-caprolactone in particular, and subsequent reaction of the polyester diols formed with diphenyl carbonate or dimethyl carbonate. Likewise suitable polycarbonate polyols B) are those which additionally contain ether groups as well as carbonate structures. These are especially the polyether carbonate polyols known per se, as obtainable, for example, by the process of EP-A 2046861 through catalytic reaction of alkylene oxides (epoxides) and carbon dioxide in the presence of H-functional starter substances.

Suitable polyacrylate polyols B) are, for example, those of the type specified in WO 2011/124710, page 10 line 32 to page 13 line 18, provided that they meet the specifications made above in terms of functionality and molecular weight. Particularly preferred polyacrylate polyols B) are polymers or copolymers of hydroxyalkyl esters of acrylic acid or methacrylic acid, for example hydroxyethyl(meth)acrylate, hydroxypropyl(meth)acrylate or hydroxybutyl(meth)acrylate, optionally together with alkyl acrylates and/or alkyl methacrylates, for example methyl(meth)acrylate, ethyl (meth)acrylate, n-butyl(meth)acrylate, isobutyl(meth)acrylate, 2-ethylhexyl(meth)acrylate, cyclohexyl(meth)acrylate, isobornyl(meth)acrylate, lauryl(meth)acrylate, styrene or other copolymerizable olefinically unsaturated monomers, for example acrylic acid, methacrylic acid or dimethyl maleate.

Suitable polyols B) are, for example, also the known polyacetal polyols obtainable through reaction of simple glycols, for example diethylene glycol, triethylene glycol, 4,4'-dioxyethoxydiphenyldimethylmethane (adduct of 2 mol of ethylene oxide onto bisphenol A) or hexanediol, with formaldehyde, or else polyacetals prepared through polycondensation of cyclic acetals, for example trioxane.

Further suitable polyols B) are, for example, also those described in EP-A 0 689 556 and EP-A 0 937 110, for example specific polyols obtainable through reaction of epoxidized fatty acid esters with aliphatic or aromatic polyols, opening the epoxide ring.

Polybutadienes containing hydroxyl groups can likewise serve as polyols B).

In a preferred embodiment of the invention, components B) used are polyether polyols, polyester polyols, polycarbonate polyols and/or polyacrylate polyols.

The polyols B) can be used individually or in the form of any desired mixtures with one another in the process according to the invention. They may either be in solvent-free form or dissolved in customary solvents.

Suitable solvents are especially those which are inert toward the isocyanate groups of component A), for example the known customary aprotic varnish solvents, for example ethyl acetate, isopropyl acetate, butyl acetate, isobutyl acetate, amyl acetate, 2-ethylhexyl acetate, ethylene glycol monomethyl ether acetate, ethylene glycol monoethyl ether acetate, ethylene glycol monobutyl ether acetate, 1-methoxyprop-2-yl acetate, 3-methoxy-n-butyl acetate, acetone, diethyl ketone, 2-butanone, 4-methyl-2-pentanone, diisobutyl ketone, cyclohexanone, cyclohexane, toluene, xylene, chlorobenzene, dichlorobenzene, petroleum spirit, aromatics having a relatively high degree of substitution, as commercially available, for example, under the Solvent naphtha, Solvesso®, Isopar®, Nappar® (Deutsche EXXON CHEMICAL GmbH, Cologne, DE) and Shellsol® (Deutsche Shell Chemie GmbH, Eschborn, DE) names, but also solvents such as propylene glycol diacetate, diethylene glycol dimethyl ether, dipropylene glycol dimethyl ether, diethylene glycol ethyl and butyl ether acetate, ethyl ethoxypropionate, propylene carbonate, N-methylpyrrolidone and N-methylcaprolactam, dioxane, tetrahydrofuran, 1,1,2,2-tetramethoxyethane or any desired mixtures of such solvents.

For performance of the process according to the invention, preferably at least a composition of compounds A) containing isocyanate groups and cyclic carbonate structures is reacted with at least one polyol B) in any sequence at temperatures of 20 to 200° C., preferably of 40 to 160° C., more preferably of 60 to 120° C., optionally in the presence of at least one of the aforementioned aprotic solvents, to give polyurethanes containing cyclic carbonate structures. In this reaction, a ratio of equivalents of isocyanate groups to hydroxyl groups of 0.3:1 to 1.2:1, preferably of 0.4:1 to 1.1:1, more preferably of 0.5:1 to 1.05:1, is observed.

The process according to the invention can be conducted without catalysis. The urethanization reaction can optionally also be accelerated using catalysts customary in isocyanate chemistry. Suitable urethanization catalysts are, for example, the compounds already described above as suitable for preparation of the composition A). These catalysts can also be used individually or in the form of any desired mixtures with one another in the process according to the invention and are used, if at all, in amounts of 0.001% to 1.0% by weight, preferably 0.01% to 0.5% by weight, calculated as the total amount of catalysts used, based on the total amount of the co-reactants A) and B).

In a preferred embodiment of the process according to the invention, the composition A) is optionally initially charged under inert gas, for example nitrogen, and optionally in the presence of a suitable solvent of the type specified, at a temperature between 20 and 100° C. Subsequently, a polyol B) or a mixture of polyols B), optionally together with another solvent, is added successively in any sequence or in a mixture in the ratio of equivalents specified above, and the reaction temperature for the urethanization, if necessary, is set to a temperature of 40 to 160° C. through a suitable measure (heating or cooling). When catalysts are used, they can be added to the composition A) and/or to the polyol component B) prior to commencement of the actual reaction. However, it is also possible to add the catalysts to the reaction mixture at any time during the urethanization reaction.

The progress of the reaction in the process according to the invention can be monitored by determining the NCO content by titrimetric means, for example, or by IR spectroscopy. After the urethanization reaction, i.e. after full conversion of isocyanate and hydroxyl groups, products obtained from the process according to the invention are the inventive polyurethanes containing cyclic carbonate structures.

The invention further provides polyurethanes containing cyclic carbonate structures, obtainable by the process according to the invention.

The inventive polyurethanes containing cyclic carbonate structures are valuable binders for production of raw materials for varnishes, sealants or adhesives.

The invention further provides for the use of the inventive polyurethanes containing cyclic carbonate structures as a starting component in the production of crosslinkable binders or of raw materials for varnishes, sealants or adhesives, and also the crosslinkable binders and raw materials for varnishes, sealants or adhesives comprising the inventive polyurethanes containing cyclic carbonate structures.

The inventive polyurethanes containing cyclic carbonate structures can be used preferentially as binders for production of raw materials of varnishes, sealants or adhesives in solvent-free form, but if required can also be diluted with customary solvents, for example the abovementioned inert varnish solvents for optional use in the process according to the invention, without causing turbidity.

While the process products of the invention based on simple alcohols and/or branched polyols, especially based on polyester polyols and/or polyacrylate polyols, are preferably suitable for conventional varnish applications, those based on high molecular weight linear polyether diols are especially used for applications in the sealants or adhesives sector.

Process products of the invention which are prepared by reacting the polyol component B) with a deficiency of isocyanate groups, especially in a ratio of equivalents of isocyanate groups to hydroxyl groups of 0.3:1 to 0.7:1, preferably of 0.4:1 to 0.6:1, more preferably of 0.45:1 to 0.55:1, can serve as the sole binders, since they have both cyclic carbonate structures and unconverted hydroxyl groups, and hence simultaneously have two mutually reactive groups.

Process products of the invention which are prepared by reacting the polyol component B) with a slight deficiency or even a slight excess of isocyanate groups, especially in a ratio of equivalents of isocyanate groups to hydroxyl groups of 0.7:1 to 1.2:1, preferably of 0.8:1 to 1.1:1, more preferably of 0.9:1 to 1.05:1, are generally crosslinked with addition of suitable hydroxy- and/or amino-functional co-reactants with which they can react to open the rings of the cyclocarbonate structures.

Suitable hydroxy-functional co-reactants for curing of the inventive polyurethanes containing cyclic carbonate structures are in principle all the compounds already mentioned above as suitable polyol components B) for preparation of these polyurethanes.

Suitable amino-functional co-reactants are, for example, any desired aliphatic and cycloaliphatic amines having at least two primary and/or secondary amino groups, for example 1,2-diaminoethane, 1,2-diaminopropane, 1,3-diaminopropane, 1,4-diaminobutane, 1,2-diamino-2-methylpropane, 1,5-diaminopentane, 1,3-diamino-2,2-dimethylpropane, 1,6-diaminohexane, 1,5-diamino-2-methylpentane, 1,6-diamino-2,2,4-trimethylhexane, 1,6-diamino-2,4,4-trimethylhexane, 1,7-diaminoheptane, 1,8-diaminooctane, 2,5-diamino-2,5-dimethylhexane, 1,9-diaminononane, 2-methyl-1,8-diaminooctane, 1,10-diaminodecane, 1,11-diaminoundecane, 1,12-diaminododecane, 1,2-diaminocyclopentane, 1,2-diaminocyclohexane, 1-amino-3,3,5-trimethyl-5-aminomethylcyclohexane (isophoronediamine, IPDA), 3(4)-aminomethyl-1-methylcyclohexylamine, 1,3-diamino-2- and/or -4-methylcyclohexane, isopropyl-2,4- and/or 2,6-diaminocyclohexane, 1,3-bis(aminomethyl)cyclohexane, 1,8-p-diaminomenthane, bis(4-aminocyclohexyl)methane, bis(4-amino-3-methylcyclohexyl)methane, bis(4-amino-3,5-dimethylcyclohexyl)methane, bis(4-amino-2,3,5-trimethylcyclohexyl)methane, 1,1-bis(4-aminocyclohexyl)propane, 2,2-bis(4-aminocyclohexyl)propane, 1,1-bis(4-aminocyclohexyl)ethane, 1,1-bis(4-aminocyclohexyl)butane, 2,2-bis(4-aminocyclohexyl)butane, 1,1-bis(4-amino-3-methylcyclohexyl)ethane, 2,2-bis(4-amino-3-methylcyclohexyl)propane, 1,1-bis(4-amino-3,5-dimethylcyclohexyl)ethane, 2,2-bis(4-amino-3,5-dimethylcyclohexyl)propane, 2,2-bis(4-amino-3,5-dimethylcyclohexyl)butane, 2,4-diaminodicyclohexylmethane, 4-aminocyclohexyl-4-amino-3-methylcyclohexylmethane, 4-amino-3,5-dimethylcyclohexyl-4-amino-3-methylcyclohexylmethane and 2-(4-aminocyclohexyl)-2-(4-amino-3-methylcyclohexyl) methane, m-xylylenediamine, methyliminobispropylamine, iminobispropylamine, bis(6-aminohexyl)amine, N,N-bis(3-aminopropyl)ethylenediamine, 4-aminomethyl-1,8-octanediamine, bis(aminopropyl)piperazine, aminoethylpiperazine, diethylenetriamine, dipropylenetriamine, triethylenetetramine, tetraethylenepentamine, pentaethylenehexamine, heptaethyleneoctamine, or any desired mixtures of such polyamines.

Suitable amino-functional co-reactants for the inventive polyurethanes containing cyclic carbonate structures are also amino-functional polyalkylene glycols, for example 1,2-bis(aminoethoxy)ethane, 1,11-diamino-3,6,9-trioxaundecane, 1,13-diamino-4,7,10-trioxatridecane, and especially the amine-functionalized polyalkylene glycols which are sold commercially under the Jeffamine® name by Huntsman Corp. and have number-average molecular weights $M_n$ of up to 5000 g/mol, preferably up to 2000 g/mol, more preferably up to 1000 g/mol.

Optionally, it is also possible to use sterically hindered aliphatic diamines having two secondary amino groups as co-reactants for the inventive polyurethanes containing cyclic carbonate structures, for example the reaction products of aliphatic and/or cycloaliphatic diamines with maleic or fumaric esters known from EP-A 0 403 921, the bis adduct of acrylonitrile onto isophoronediamine obtainable according to the teaching of EP-A 1 767 559, or the hydrogenation products of Schiff bases obtainable from aliphatic and/or cycloaliphatic diamines and ketones, for example diisopropyl ketone, described in DE-A 19 701 835 for example.

Further polyamines suitable as co-reactants for the inventive process products are additionally also the polyamido amines, polyimines and/or polyvinylamines known as crosslinker components for epoxy resins.

Finally, suitable co-reactants for the inventive process products are also amino alcohols, for example 2-aminoethanol, the isomeric aminopropanols and -butanols, 3-aminopropane-1,2-diol and 1,3-diamino-2-propanol.

In the formulation of varnishes, sealants or adhesives from the inventive polyurethanes containing cyclic carbonate structures, the hydroxy- and/or amino-functional co-reactants specified are added either as individual compounds or in the form of any desired mixtures with one another, generally in such amounts that there are from 0.7 to 1.5, preferably from 0.8 to 1.2 and more preferably 0.9 to 1.1 hydroxyl and/or amino groups for each cyclocarbonate structure.

The varnishes, sealants or adhesives produced from the inventive polyurethanes containing cyclic carbonate structures can be cured over a wide temperature range, for example from −20° C. to 250° C., preferably from 0° C. to 200° C., without catalysis or in the presence of suitable catalysts. While the reaction with aminic co-reactants generally proceeds with sufficient speed even at low temperatures and without addition of catalyst, curing with alcoholic co-reactants generally requires higher temperatures and frequently the additional use of suitable catalysts for complete crosslinking. Suitable catalysts for the curing of the inventive polyurethanes containing cyclic carbonate structures with hydroxy- and/or amino-functional co-reactants are, for example, the compounds already described above as being suitable for preparation of the compounds A) containing isocyanate groups and cyclic carbonate structures. Further compounds likewise suitable as catalysts are additionally also the organometallic compounds and metal carboxylates specified as catalysts in EP-A 0 911 352, and also the bases with conjugate acids having a pKa of 13 or more described in EP-A 0 983 231, especially the hydroxides, alkoxides and/or N,N-bis(trimethylsilyl)amidates specified therein.

These catalysts can be used individually or in the form of any desired mixtures with one another and are used, if at all, in amounts of 0.001% to 3.0% by weight, preferably 0.01% to 1.0% by weight, calculated as the total amount of catalysts used, based on the total amount of inventive polyurethanes containing cyclic carbonate structures and any alcoholic and/or aminic co-reactants used.

In the case of formulation of varnishes, sealants or adhesives, the inventive polyurethanes containing cyclic carbonate structures can also be supplemented with any desired further auxiliaries and additives, for example the customary UV stabilizers, antioxidants, water scavengers, slip additives, defoamers, leveling agents, rheology additives, flame retardants, fillers and/or pigments.

The coatings, sealants or adhesives formulated using the inventive polyurethanes containing cyclic carbonate structures can be applied by methods known per se, for example by spraying, painting, dipping, flow-coating, or with the aid of rollers or film coaters, in one or more layers. Possible substrates are any desired substrates, for example metal, wood, glass, stone, ceramic materials, concrete, hard and flexible plastics, textiles, leather and paper, which may optionally also be provided with customary primers prior to coating.

EXAMPLES

The invention is illustrated in detail hereinafter by examples.

All percentages are based on weight, unless stated otherwise.

The NCO contents are determined by titrimetric means to DIN EN ISO 11909.

OH numbers were determined by titrimetric means to DIN 53240-2: 2007-11, acid numbers to DIN 3682. The OH contents reported were calculated from the OH numbers determined by analysis.

The residual monomer contents were measured to DIN EN ISO 10283 by gas chromatography with an internal standard.

The proportions of bis adduct (formed from two molecules of hydroxy-functional cyclic carbonate and one molecule of diisocyanate) were determined by gel permeation chromatography based on DIN 55672-1 (Gel permeation chromatography (GPC)—Part 1: Tetrahydrofuran (THF) as elution solvent), with the alteration that a flow rate of 0.6 ml/min rather than 1.0 ml/min was employed. The proportions of bis adduct in area % taken from the chromatograms were each equated approximately to proportions in % by weight and reported as such, based on the total amount of mono adduct and bis adduct.

All the viscosity measurements were made with a Physica MCR 51 rheometer from Anton Paar Germany GmbH (DE) to DIN EN ISO 3219.

The melting ranges reported were determined with the aid of a Kofler hot bench from Wagner & Munz GmbH (DE).

Starting Compounds
Preparation of the Compositions A)
Composition A1)

1680 g (10 mol) of hexamethylene diisocyanate (HDI) were initially charged under dry nitrogen at a temperature of 100° C., 118 g (1 mol) of glycerol carbonate were added within 30 minutes and the mixture was stirred for a further 5 hours until an NCO content of 44.4%, corresponding to full urethanization, had been attained. Subsequently, the unconverted monomeric HDI was removed on a thin-film evaporator at a temperature of 140° C. and a pressure of 0.1 mbar. This gave a virtually colorless, clear isocyanate-functional cyclic carbonate which gradually crystallized through at room temperature within one week.

The product had the following characteristic data:

| NCO content: | 14.1% |
|---|---|
| Monomeric HDI: | 0.19% |
| Melting range: | 28-30° C. |
| Proportion of bis adduct: | 3.8% |

Composition A2)

By the process described for composition A1), 1776 g (8 mol) of isophorone diisocyanate (IPDI) were reacted with 118 g (1 mol) of glycerol carbonate. On attainment of an NCO content of 33.3%, corresponding to full urethanization, the unconverted monomeric IPDI was removed by thin-film distillation at a temperature of 160° C. and a pressure of 0.2 mbar, and an isocyanate-functional cyclic carbonate was obtained in the form of a clear, pale yellow solid resin.

| NCO content: | 11.8% |
|---|---|
| Monomeric IPDI: | 0.21% |
| Proportion of bis adduct: | 4.5% |

Composition A3)

By the process described for composition A1), 2096 g (8 mol) of 4,4'-diisocyanatodicyclohexylmethane ($H_{12}$-MDI) were reacted with 118 g (1 mol) of glycerol carbonate. On attainment of an NCO content of 28.5%, corresponding to full urethanization, the unconverted monomeric $H_{12}$-MDI was removed by thin-film distillation at a temperature of 170° C. and a pressure of 0.2 mbar, and an isocyanate-functional cyclic carbonate was obtained in the form of a clear, pale yellow solid resin.

| NCO content: | 10.3% |
|---|---|
| Monomeric H12-MDI: | 0.28% |
| Proportion of bis adduct: | 4.6% |

Composition A4)

By the process described for composition A1), 1344 g (8 mol) of HDI were reacted with 160 g (1 mol) of TMP carbonate. On attainment of an NCO content of 41.9%, corresponding to full urethanization, the unconverted monomeric HDI was removed by thin-film distillation at a temperature of 160° C. and a pressure of 0.2 mbar, and a clear, almost colorless isocyanate-functional cyclic carbonate was obtained with the following characteristic data:

| NCO content: | 12.1% |
|---|---|
| Monomeric HDI: | 0.17% |
| Viscosity (23° C.): | 77 000 mPas |
| Proportion of bis adduct: | 5.1% |

Composition A5)

By the process described for composition A1), 672 g (4 mol) of HDI were reacted with 118 g (1 mol) of glycerol carbonate. On attainment of an NCO content of 37.2%, corresponding to full urethanization, the unconverted monomeric HDI was removed by thin-film distillation as described in example 1, and a clear, virtually colorless isocyanate-functional cyclic carbonate was obtained, which gradually crystallized through at room temperature within one week.

The product had the following characteristic data:

| NCO content: | 13.4% |
|---|---|
| Monomeric HDI: | 0.11% |
| Melting range: | 27-30° C. |
| Proportion of bis adduct: | 9.1% |

Composition A6) (Comparison)

By the process described for composition A1), 504 g (3 mol) of HDI were reacted with 118 g (1 mol) of glycerol carbonate. On attainment of an NCO content of 33.8%, corresponding to full urethanization, the unconverted monomeric HDI was removed by thin-film distillation as described in example 1, and a clear, virtually colorless isocyanate-functional cyclic carbonate was obtained, which partly crystallized after being cooled to room temperature.

The product had the following characteristic data:

| | |
|---|---|
| NCO content: | 12.7% |
| Monomeric HDI: | 0.19% |
| Proportion of bis adduct: | 13.5% |

Polyols B

Polyol B1

Polyacrylate polyol dissolved in a concentration of 70% in butyl acetate, prepared from 33.0% hydroxyethyl methacrylate, 24.3% n-butyl acrylate, 38.8% styrene, 0.9% acrylic acid and 3.0% di-tert-butyl peroxide.

| | |
|---|---|
| OH number (OH content) | 98 mg KOH/g (3.0%) |
| Equivalent weight: | 572 g/eq OH |
| Acid number: | 7.5 mg KOH/g |
| Viscosity (23° C.): | 3500 mPas |

Polyol B2)

Solvent-free polyester polyol, prepared from 11.9% adipic acid, 33.7% isophthalic acid, 10.7% trimethylolpropane, 37.7% hexane-1,6-diol and 6.0% phthalic anhydride.

| | |
|---|---|
| OH number (OH content) | 143 mg KOH/g (4.3%) |
| Equivalent weight: | 392 g/eq OH |
| Acid number: | 1 mg KOH/g |
| Viscosity (23° C.): | 2500 mPas (as 80% solution in butyl acetate) |

Polyol B3)

Polyester polyol dissolved in a concentration of 75% in Solvent naphtha 100, prepared from 19.2% adipic acid, 22.3% maleic anhydride, 4.6% trimethylolpropane, 1.7% propane-1,2-diol and 40.2% neopentyl glycol.

| | |
|---|---|
| OH number (OH content) | 68 mg KOH/g (2.0%) |
| Equivalent weight: | 825 g/eq OH |
| Acid number: | 3 mg KOH/g |
| Viscosity (23° C.): | 3700 mPas |

Example 1

Inventive and Comparative 297.9 g (1.0 eq) of composition A1) were diluted with 524.3 g of butyl acetate, 565.6 g (1.0 eq) of polyol B1) were added at a temperature of 80° C. under dry nitrogen, and then the mixture was stirred at 90° C. for 8 hours until no isocyanate was detectable any longer by IR spectroscopy. After cooling to room temperature, an inventive polyurethane containing cyclic carbonate structures was present in the form of a colorless solution.

| | |
|---|---|
| Solids content: | 50% |
| Viscosity (23° C.): | 1370 mPas |
| Equivalent weight: | 1387.8 g/eq of cyclic carbonate |

For comparison, 1680 g (10 mol) of hexamethylene diisocyanate (HDI) were admixed with 283 g (0.5 eq) of polyol B1) at a temperature of 80° C. under dry nitrogen within 20 minutes. The temperature was then increased to 100° C. and stirring of the reaction mixture continued until, after 2 hours, an NCO content of 41.7%, corresponding to full urethanization, had been attained. An attempt to remove the unconverted excess monomeric HDI together with the butyl acetate originating from polyol B1) by thin-film distillation was unsuccessful. At a temperature of 140° C. and a pressure of 0.1 mbar, a solid, non-free-flowing resin formed on the evaporator surface.

The comparison shows that it is not possible to use polyol B1) and HDI to prepare a low-monomer isocyanate-functional prepolymer which could be reacted with glycerol carbonate to give a polyurethane containing cyclic carbonate structures similarly to that obtained in accordance with the invention.

Example 2

Inventive 282 g (0.9 mol) of composition A5) were initially charged under dry nitrogen in 215 g of 1,1,2,2-tetramethoxyethane as solvent at a temperature of 80° C., 40 g (0.3 mol) of trimethylolpropane (TMP) were added in portions within 20 min, and the mixture was stirred for a further 4 hours until the isocyanate band in the IR spectrum disappeared completely. After cooling to room temperature, an inventive polyurethane containing cyclic carbonate structures was present in the form of a colorless solution.

| | |
|---|---|
| Solids content: | 60% |
| Viscosity (23° C.): | 5220 mPas |
| Equivalent weight: | 596.7 g/eq of cyclic carbonate |

Example 3

Comparative 298 g (0.9 mol) of the noninventive composition A6) were initially charged under dry nitrogen in 225 g of 1,1,2,2-tetramethoxyethane as solvent at a temperature of 80° C., 40 g (0.3 mol) of trimethylolpropane (TMP) were added in portions within 20 min, and the mixture was stirred for a further 4 hours until the isocyanate band in the IR spectrum disappeared completely. The 60% solution of a polyurethane bearing terminal cyclocarbonate groups that was present turned very cloudy immediately after being cooled down to room temperature and formed a conspicuous sediment within a few days.

The comparison with the reaction product of the inventive composition A5) with TMP, obtained as a clear solution according to example 2), shows that composition A6), which was prepared using a smaller excess of isocyanate groups than the minimum according to the invention, is not crystallization-stable because of an excessively high proportion of bis adduct and hence is unsuitable for preparation of polyurethanes bearing cyclocarbonate groups.

Example 4

Inventive 355.9 g (1.0 eq) of composition A2) were diluted with 582.3 g of butyl acetate, 565.6 g (1.0 eq) of polyol B1) were added at a temperature of 80° C. under dry nitrogen, and then the mixture was stirred at 100° C. for 20 hours until no isocyanate was detectable any longer by IR spectroscopy. After cooling to room temperature, an inventive polyurethane containing cyclic carbonate structures was present in the form of a virtually colorless solution.

| | |
|---|---|
| Solids content: | 50% |
| Viscosity (23° C.): | 1510 mPas |
| Equivalent weight: | 1503.8 g/eq of cyclic carbonate |

Example 5

Inventive 355.9 g (1.0 eq) of composition A2) were diluted with 651.8 g of butyl acetate, 493.3 g (1.0 eq) of an 80% solution of polyol B2) in butyl acetate were added at a temperature of 80° C. under dry nitrogen, and then the mixture was stirred at 100° C. for 20 hours until no isocyanate was detectable any longer by IR spectroscopy. After cooling to room temperature, an inventive polyurethane containing cyclic carbonate structures was present in the form of a virtually colorless solution.

| | |
|---|---|
| Solids content: | 50% |
| Viscosity (23° C.): | 1490 mPas |
| Equivalent weight: | 1501.0 g/eq of cyclic carbonate |

Example 6

Inventive 297.9 g (1.0 eq) of composition A1) were diluted with 722.2 g of Solvent naphtha 100, 848.5 g (1.0 eq) of polyol B3) were added at a temperature of 80° C. under dry nitrogen, and then the mixture was stirred at 90° C. for 8 hours until no isocyanate was detectable any longer by IR spectroscopy. After cooling to room temperature, an inventive polyurethane containing cyclic carbonate structures was present in the form of a virtually colorless solution.

| | |
|---|---|
| Solids content: | 50% |
| Viscosity (23° C.): | 1860 mPas |
| Equivalent weight: | 1868.6 g/eq of cyclic carbonate |

Example 7

Inventive 355.9 g (1.0 eq) of composition A2) were diluted with 780.2 g of Solvent naphtha 100, 848.5 g (1.0 eq) of polyol 83) were added at a temperature of 80° C. under dry nitrogen, and then the mixture was stirred at 100° C. for 20 hours until no isocyanate was detectable any longer by IR spectroscopy. After cooling to room temperature, an inventive polyurethane containing cyclic carbonate structures was present in the form of a virtually colorless solution.

| | |
|---|---|
| Solids content: | 50% |
| Viscosity (23° C.): | 1980 mPas |
| Equivalent weight: | 1984.6 g/eq of cyclic carbonate |

Example 8

Inventive 407.8 g (1.0 eq) of composition A3) were diluted with 634.2 g of butyl acetate, 565.6 g (1.0 eq) of polyol B1) were added at a temperature of 80° C. under dry nitrogen, and then the mixture was stirred at 100° C. for 20 hours until no isocyanate was detectable any longer by IR spectroscopy. After cooling to room temperature, an inventive polyurethane containing cyclic carbonate structures was present in the form of a pale yellow solution.

| | |
|---|---|
| Solids content: | 50% |
| Viscosity (23° C.): | 2540 mPas |
| Equivalent weight: | 1607.6 g/eq of cyclic carbonate |

Example 9

Inventive 347.1 g (1.0 eq) of composition A4) were diluted with 573.5 g of butyl acetate, 565.6 g (1.0 eq) of polyol B1) were added at a temperature of 80° C. under dry nitrogen, and then the mixture was stirred at 90° C. for 8 hours until no isocyanate was detectable any longer by IR spectroscopy. After cooling to room temperature, an inventive polyurethane containing cyclic carbonate structures was present in the form of a colorless solution.

| | |
|---|---|
| Solids content: | 50% |
| Viscosity (23° C.): | 1420 mPas |
| Equivalent weight: | 1486.2 g/eq of cyclic carbonate |

Example 10

Inventive, Self-Crosslinker 149.0 g (0.5 eq) of composition A1) were diluted with 193.7 g of butyl acetate, 565.6 g (1.0 eq) of polyol B1) were added at a temperature of 80° C. under dry nitrogen, and then the mixture was stirred at 90° C. for 8 hours until no isocyanate was detectable any longer by IR spectroscopy. After cooling to room temperature, an inventive polyurethane that contained cyclic carbonate structures and was simultaneously hydroxy-functional was present in the form of a colorless solution.

| | |
|---|---|
| Solids content: | 60% |
| Viscosity (23° C.): | 2370 mPas |
| Equivalent weight: | 1816.6 g/eq of cyclic carbonate |
| Equivalent weight: | 1816.6 g/eq OH |

Example 11-16

Use, Inventive

The inventive polyurethanes 1), 4), 5) and 7) containing cyclic carbonate structures were used to formulate varnishes together with the amino-functional co-reactants listed in table 1, and each was adjusted to a solids content of 50%. The varnishes were applied to glass panes in a wet film thickness of about 100 μm, flashed off at room temperature for 15 minutes and dried at 70° C. or 120° C. for 30 min. In all cases, shiny transparent varnish films were obtained. Table 1 below shows the compositions of the varnish formulations (parts by weight in each case) and properties of the resultant coatings.

TABLE 1

| Example | 11 | 12 | 13 | 14 | 15 | 16 |
|---|---|---|---|---|---|---|
| Polyurethane from example 1 | 82.6 | — | — | — | — | — |
| Polyurethane from example 4 | — | 83.6 | — | — | — | — |
| Polyurethane from example 5 | — | — | 83.6 | 88.8 | — | — |
| Polyurethane from example 7 | — | — | — | — | 87.2 | 91.2 |
| Jeffamin ® T 403 [1] | 8.7 | 8.2 | 8.2 | — | 6.4 | 4.4 |
| tetraethylene-pentamine [2] | — | — | — | 5.6 | — | — |
| butyl acetate | 8.7 | 8.2 | 8.2 | 5.6 | — | — |
| Solvent Naphtha 100 | — | — | — | — | 6.4 | 4.4 |
| Crosslinking temperature (° C.) | 120 | 120 | 120 | 70 | 70 | 120 |
| Appearance of film | OK | OK | OK | OK | OK | OK |
| Layer thickness (μm) | 50 | 45 | 45 | 50 | 50 | 45 |
| Pendulum hardness (s) after 24/48 h [3] | 47/48 | 114/129 | 116/131 | 112/193 | 87/100 | 166/209 |
| Acetone resistance [4] | 1 | 1-2 | 2-3 | 1 | 2 | 1-2 |

[1] Trifunctional polyetheramine (Huntsman Corp., Zaventem, Belgium), equivalent weight: 146.7 g/eq of amine
[2] Equivalent weight: 94.7 g/eq of amine (based on primary amino groups)
[3] König pendulum hardness (DIN 53157)
[4] Resistance of the cured varnish film to acetone after a contact time of 1 min. Rating: 0-5 (0 = varnish film unchanged; 1 = visible change; 2 = perceptible softening; 3 = significant softening; 4 = softened through to the substrate; 5 = completely destroyed without any outside influence)

Examples 17

Use, Self-Crosslinker 100 parts by weight of the inventive polyurethane that contained cyclic carbonate structures and simultaneously hydroxyl groups from example 10) were admixed with 0.5 part by weight of sodium laurate as catalyst, adjusted to a solids content of 50% by addition of 20 parts by weight of butyl acetate and then applied to a glass pane in a wet film thickness of about 100 μm. After flashing off at room temperature for 15 minutes, the varnish was baked at 160° C. for 30 min. A shiny transparent varnish film was obtained. The pendulum hardness was 66 s after 24 h; the acetone resistance was 1-2 (rating as in table 1, defined in footnote [4]).

The invention claimed is:

1. A process for preparing polyurethanes containing cyclic carbonate structures, comprising reacting at least
    A) a composition comprising
        a) a compound of the general formula (I) containing one or more isocyanate groups and cyclic carbonate structures $$R-X-O-\underset{\underset{O}{\parallel}}{C}-\underset{\underset{H}{|}}{N}-Y-NCO \quad (CH_2)_n \quad (I)$$

(with cyclic carbonate group)

b) ≤1% by weight, based on the total mass of the composition A), of one or more monomeric diisocyanate having aliphatically, cycloaliphatically, araliphatically and/or aromatically bonded isocyanate groups of the general formula (II), $$OCN-Y-NCO \quad (II)$$

and
        c) 0.5% to 12% by weight, based on the total mass of components a) and c) of compounds of the general formula (III)

$$R-X-O-\underset{\underset{O}{\parallel}}{C}-\underset{\underset{H}{|}}{N}-Y-\underset{\underset{H}{|}}{N}-\underset{\underset{O}{\parallel}}{C}-O-X-R \quad (III)$$

(with cyclic carbonate groups on both sides)

wherein, independently, for each of a), b) and c),
    R is hydrogen or a saturated or unsaturated, linear or branched, aliphatic radical having 1 to 7 carbon atoms,
    X is a linear or branched organic radical which has 1 to 36 carbon atoms and which may optionally contain ether, ester and/or carbonate groups,
    n is 0 or 1 and
    Y is a linear or branched, aliphatic or cycloaliphatic radical having 4 to 18 carbon atoms or an optionally substituted aromatic or araliphatic radical having 6 to 18 carbon atoms,
with
    B) an at least difunctional polyol having a number-average molecular weight $M_n$ of 62 to 22 000 g/mol,
while maintaining a ratio of equivalents of isocyanate groups to hydroxyl groups of 0.3:1 to 1.2:1.

2. The process for preparing polyurethanes containing cyclic carbonate structures as claimed in claim 1, wherein composition A) contains
    a) ≥88% by weight of the compound of the general formula (I),
    b) ≤1% by weight of one or more monomeric diisocyanate having aliphatically, cycloaliphatically, araliphatically and/or aromatically bonded isocyanate groups of the general formula (II), and
    c) ≤12% by weight of the compound of the general formula (III), where the proportion of each of a) and c) relates to the total mass of the compounds a) and c), and the proportion of b) relates to the total mass of the composition A), and where
- R is hydrogen or a saturated or unsaturated, linear or branched, aliphatic radical having 1 to 7 carbon atoms,
- X is a linear or branched organic radical which has 1 to 36 carbon atoms and which may optionally contain ether, ester and/or carbonate groups,
- n is 0 or 1 and
- Y is a linear or branched, aliphatic or cycloaliphatic radical having 4 to 18 carbon atoms or an optionally substituted aromatic or araliphatic radical having 6 to 18 carbon atoms.

3. The process as claimed in claim 1, characterized in that, for the formulae (I) and (II) of components a) and b), or for the formulae (I), (II) and (III) of components a), b) and c),
- Y is a linear or branched, aliphatic or cycloaliphatic radical having 6 to 13 carbon atoms.

4. The process as claimed in claim 1, wherein, for the formula (I) of component a) or the formulae (I) and (III) of components a) and c),
- R is hydrogen or a saturated linear aliphatic radical having 1 or 2 carbon atoms,
- X is a linear or branched organic radical which has 1 to 18 carbon atoms and which may optionally contain ether, ester and/or carbonate groups, and
- n is 0 or 1.

5. The process as claimed in claim 1, wherein, for the formula (I) of component a) or the formulae (I) and (III) of components a) and c),
- R is hydrogen or a saturated linear aliphatic radical having 1 or 2 carbon atoms,
- X is a methylene group (—CH2-) and
- n is 0 or 1.

6. The process as claimed in claim 1, wherein the polyol component B) has a mean functionality of 2 to 6.

7. The process as claimed in claim 1, wherein component B) is a polyhydric alcohol, a ether alcohol or an ester alcohols and/or polymeric polyol, said polymeric polyol having a number-average molecular weight $M_n$ of 200 to 22 000 g/mol.

8. The process as claimed in claim 7, wherein component B) is a polyhydric alcohol and/or a ether alcohol or an ester alcohol containing 2 to 14 carbon atoms.

9. The process as claimed in claim 7, wherein component B) is a polyether polyol, a polyester polyol, a polycarbonate polyol and/or a polyacrylate polyol.

10. A polyurethanes containing cyclic carbonate structures, obtained by the process as claimed in claim 1.

11. A method for the production of crosslinkable binders comprising utilizing the polyurethanes containing cyclic carbonate structures as claimed in claim 10 as a starting component.

12. A method for the production of crosslinkable raw materials for varnishes, sealants or adhesives comprising utilizing the polyurethanes containing cyclic carbonate structures as claimed in claim 10 as a starting component.

13. A crosslinkable binder comprising polyurethanes containing cyclic carbonate structures as claimed in claim 10.

14. The process as claimed in claim 1, wherein component B) comprises an at least difunctional polyol having a number-average molecular weight $M_n$ of 90 to 12000 g/mol.

15. The process as claimed in claim 1, wherein component A) contains component c) in an amount of 0.5% to 10% by weight, based on the total mass of components a) and c).

16. The process as claimed in claim 1, wherein the polyol component B) has a mean functionality of 2 to 4.

* * * * *